United States Patent [19]
Baker et al.

[11] Patent Number: 6,136,569
[45] Date of Patent: Oct. 24, 2000

[54] METHOD OF CREATING A CDNA LIBRARY ENRICHED IN SIGNAL SEQUENCES

[75] Inventors: Kevin Baker, San Mateo; Austin Gurney, Belmont, both of Calif.

[73] Assignee: Genentech, Inc., South San Francisco, Calif.

[21] Appl. No.: 08/815,520

[22] Filed: Feb. 27, 1997

[51] Int. Cl.$^7$ .............................. C12N 15/65; C12P 19/34
[52] U.S. Cl. ...................................... 435/91.41; 435/91.51
[58] Field of Search ............................... 435/91.41, 91.51

[56] References Cited

U.S. PATENT DOCUMENTS

| | | |
|---|---|---|
| 4,914,025 | 4/1990 | Manoil et al. . |
| 5,212,070 | 5/1993 | Smith et al. ............................ 435/69.1 |
| 5,498,832 | 3/1996 | Gausing et al. . |
| 5,536,637 | 7/1996 | Jacobs . |

FOREIGN PATENT DOCUMENTS

| | | |
|---|---|---|
| 244042 | 11/1987 | European Pat. Off. . |
| 307247 | 3/1989 | European Pat. Off. . |
| 607054 A2 | 7/1994 | European Pat. Off. . |

OTHER PUBLICATIONS

Alam et al., "Reporter Genes: Application to the Study of Mammalian Gene Transcription" *Analytical Biochemistry* 188:245–254 (1990).

Ausubel et al., "Units 1.10–1.11 and Unit 1.15.7" *Current Protocols in Molecular Biology*, John Wiley and Sons (1991).

Ausubel et al., "Units 2.2–2.4, 3, 5.1.1–5.1.2, 5.2.1, 5.3.2–5.3.6, 5.4.1–5.4.3, 5.5.2–5.5.7, 5.6.1–5.6.8, 5.7.1–5.7.3, 5.8.1–5.8.11 and 9.3" *Current Protocols in Molecular Biology*, John Wiley & Sons, Inc. (1995).

Biely et al., "A New Chromogenic Substrates for Assay and Detection of α–Amylase" *Analytical Biochemistry* 172:176–179 (1988).

Bui et al., "Cloning and Expression of an Arxula Adeninivorans Glucoamylase Gene in *Saccharomyces cerevisiae*" *Appl. Microbiol. Biotechnol.* 44:610–619 (1996).

Clarke et al., "A Colony Bank Containing Synthetic Col El Hybrid Plasmids Representative of the Entire *E. coli* Genome" *Cell* 9:91–99 (Sep. 1976).

Clementi et al., "α–Amylase and Glucoamylase Production by *Schwanniomyces castellii*" *Antonie van Leeuwenhoek* 52:343–352 (1986).

Felgner et al., "Lipofection: A Highly Efficient, Lipid–Mediated DNA–Transfection Procedure" *Proc. Natl. Acad. Sci. USA* 84:7413–7417 (Nov. 1987).

Gietz et al., "Improved Method for High Efficiency Transformation of Intact Yeast Cells" *Nucl. Acid. Res.* 20(6):1425 (1992).

Gubler et al., "A Simple and Very Efficient Method for Generating cDNA Libraries" *Gene* 25:263–269 (1983).

Jacobs et al., "A Novel Method for Isolating Eukaryotic cDNA Clones Encoding Secreted Proteins" *J. Cell. Biochem.* (Abstract C1–207) Supp. 21A:19 (Mar. 1995).

Jensen et al., "*Bacillus acidopullulyticus* Pullulanase: Application and Regulatory Aspects for Use in the Food Industry" *Process Biochem.* 19:129–134 (Aug. 1984).

Kaiser et al., "Many Random Sequences Functionally Replace the Secretion Signal Sequence of Yeast Invertase" *Science* 235:312–317 (Jan. 16, 1987).

Kaiser et al., "Media (Appendix A)" *Methods in Yeast Genetics*, Cold Spring Harbor, N.Y.:Cold Spring Harbor Press pp. 207–210 (1994).

Kaiser et al., "Secretion–Defective Mutations in the Signal Sequence for *Saccharomyces cerevisiae* Invertase" *Molecular & Cellular Biology* 6(7):2382–2391 (Jul. 1986).

Kato et al., "Construction of a Human Full–Length cDNA Bank" *Gene* 150:243–250 (1994).

Klein et al., "Selection for Genes Encoding Secreted Proteins and Receptors" *Proc. Natl. Acad. Sci. USA* 93:7108–7113 (Jul. 1996).

Lopata et al., "High Level Transient Expression of a Chloramphenicol Acetyl Transferase Gene by DEAE–Dextran Mediated DNA Transfection Coupled with a Dimethyl Sulfoxide or Glycerol Shock Treatment" *Nucleic Acids Research* 12(14):5707 (1984).

Mandel et al., "Calcium–dependent Bacteriophage DNA Infection" *J. Mol. Biol.* 53:159–162 (1970).

Manners, D., "Recent Developments in Our Understanding of Amylopectin Structure" *Carbohydr. Pol.* 11:87–112 (1989).

McCann et al., "The Utilization of Starch by Yeasts" *Yeast* 2:109–115 (1986).

Messing et al., "Filamentous Coliphage M13 as a Cloning Vehicle: Insertion of a HindII Fragment of the lac Regulatory in M13 Replicative Form in vitro" *Proc. Natl. Acad. Sci. USA* 74(9):3642–3646 (Sep. 1977).

Messing, J., "New M13 Vectors for Cloning" *Methods in Enzymology*, Academic Press vol. 101:20–78 (1983).

Miller et al., "High–Voltage Electroporation of Bacteria: Genetic Transformation of Campylobacter Jejuni with plasmid DNA" *Proc. Natl. Acad. Sci. USA* 85:856–860 (Feb. 1988).

Modena et al., "Biochemical and Immunological Characterization of the STA2–Encoded Extracellular Glucoamylase from *Saccharomyces Diastaticus*" *Arch. Bioch. Biophys.* 248(1):138–150 (Jul. 1986).

Nakamura et al., "Sequences of cDNAs for Human Salivary and Pancreatic α–Amylase" *Gene* 28:263–270 (1984).

(List continued on next page.)

*Primary Examiner*—Terry McKelvey
*Attorney, Agent, or Firm*—Craig G. Svoboda

[57] ABSTRACT

The present invention relates to a novel method of identifying cDNA's which encode secreted and membrane-bound proteins. The present invention also relates to a novel method for preparing cDNA libraries enriched for signal sequences. The methods of the invention provide for an improved signal sequence detection system which results, when compared to the prior art, in a greater number of correctly identified signal sequences and less total time required to complete the procedure.

8 Claims, 3 Drawing Sheets

OTHER PUBLICATIONS

Nishide et al., "Corrected Sequences of cDNAs for Human Salivary and Pancreatic α–Amylase" *Gene* 50:371–372 (1986).

Okayama et al., "High–Efficiency Cloning of Full–Length cDNA" *Molecular & Cellular Biology* 2(2):161–170 (Feb. 1982).

Rothstein, R., "Targeting, Disruption, Replacement, and Allele Rescue: Integrative DNA Transformation in Yeast" *Methods Enzymol.*, Academic Press vol. 194:281–301 (1991).

Sambrook et al. *Molecular Cloning: A Laboratory Manual*, Second Edition edition, New York:Cold Spring Harbor Laboratory Press (1989).

Seed et al., "Representation of DNA Sequences in Recombinant DNA Libraries Prepared by Restriction Enzyme Partial Digestion" *Gene* 19:201–209 (1982).

Shibuya et al., "Cloning of the α–Amylase cDNA of *Aspergillus shirousamii* and Its Expression in *Saccharomyces cerevisiae*" *Biosci. Biotech. Biochem.* 56(2):174–179 (1992).

Shibuya et al., "Molecular Cloning of the Glucoamylase Gene of *Aspergillus shirousami* and Its Expression in *Aspergillus oryzae*" *Agric. Biol. Chem.* 54(8):1905–1914 (1990).

Shigekawa et al., "Electroporation of Eukaryotes and Prokaryotes: A General Approach to the Introduction of Macromolecules into Cells" *BioTechniques* 6(8):742–751 (1988).

Soloman, B., "Starch Hydrolysis by Immobilized Enzymes Industrial Applications" *Advances in Biochemical Engineering*, New York:Springer Berlin Heidelberg vol. 10:131–177 (1978).

Vieira et al., "Production of Single–stranded Plasmid DNA" *Methods in Enzymology* 153:3–11 (1987).

von Heijne, G., "The Signal Peptide" *J. Membrane Biol.* 115:195–201 (1990).

von Heijne, G., "Signal Sequences: The Limits of Variation" *J. Mol. Biol.* 184:99–105 (1985).

Yanisch–Perron et al., "Improved M13 Phage Cloning Vectors and Host Strains: Nucleotide Sequences of the M13mp18 and pUC19 Vectors" *Gene* 33:103–119 (1985).

METHOD OF CREATING A CDNA LIBRARY ENRICHED IN SIGNAL SEQUENCES

BACKGROUND OF THE INVENTION

The present invention relates to a novel method of identifying nucleic acid encoding secreted and membrane-bound proteins based upon the presence of signal sequences. The present invention also relates to a novel method for preparing cDNA libraries enriched for signal sequences.

Extracellular proteins are essential in the formation, differentiation and maintenance of multicellular organisms. The determination by individual cells of whether to live, proliferate, migrate, differentiate, interact with other cells or secrete are governed by information received from the cells neighbors and the immediate environment. This information is often transmitted by secreted polypeptides (e.g., mitogenic factors, survival factors, cytotoxic factors, differentiation factors, neuropeptides, and hormones) which are in turn received and interpreted by diverse cell receptors. These secreted polypeptides or signaling molecules normally pass through the cellular secretory pathway to reach their site of action in the extracellular environment.

The targeting of both secreted and transmembrane proteins to the secretory pathway is accomplished via the attachment of a short, amino-terminal sequence, known as the signal peptide or signal sequence. von Heijne, G. (1985) *J. Mol. Biol.* 184, 99–105; Kaiser, C. A. & Botstein, D. (1986), *Mol. Cell. Biol.* 6, 2382–2391. The signal peptide itself contains several elements necessary for optimal function, the most important of which is a hydrophobic component. Immediately preceding the hydrophobic sequence is often a basic amino acid or acids, whereas at the carboxyl-terminal end of the signal peptide are a pair of small, uncharged amino acids separated by a single intervening amino acid which defines the signal peptidase cleavage site. While the hydrophobic component, basic amino acid and peptidase cleavage site can usually be identified in the signal peptide of known secreted proteins, the high level of degeneracy within any one of these elements makes difficult the identification or isolation of secreted or transmembrane proteins solely by searching for signal peptides in DNA data bases (e.g. GeneBank, GenPept), or based upon hybridization with DNA probes designed to recognize cDNA's encoding signal peptides.

Secreted and membrane-bound cellular proteins have wide applicability in various industrial applications, including pharmaceuticals, diagnostics, biosensors and bioreactors. For example, most protein drugs commercially available at present, such as thrombolytic agents, interferons, interleukins, erythropoietins, colony stimulating factors, and various other cytokines are secretory proteins. Their receptors, which are membrane proteins, also have potential as therapeutic or diagnostic agents. Significant resources are presently being expended by both industry and academia to identify new native secreted proteins.

According to a screening method recently reported by Klein R. D. et al. (1996), *Proc. Natl. Acad. Sci.* 93, 7108–7113 and Jacobs (U.S. Pat. No. 5,536,637 issued Jul. 16, 1996), cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein R. D., supra, and Jacobs, supra, take advantage of the known ability of mammalian signal sequences to functionally replace the native signal sequence of yeast invertase. A mammalian cDNA library is ligated to a DNA encoding a nonsecreted yeast invertase, the ligated DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length cDNA library to isolate the full-length clones encoding the corresponding secreted proteins.

Given the great efforts presently being expended to discover novel secreted and transmembrane proteins as potential therapeutic agents, there is a great need for an improved system which can simply and efficiently identify the coding sequences of such proteins in mammalian recombinant DNA libraries. While effective, the invertase yeast selection process described above has several disadvantages. First, it requires the use of special yeast cells in which the SUC2 gene encoding the invertase protein has been deleted or the coding sequence of the native invertase signal has been mutated so that the invertase is not secreted. Second, even invertase-deficient yeast may grow on sucrose or raffinose, albeit at a low rate, therefore, the invertase selection may need to be repeated several times to improve the selection for transformants containing the signal-less yeast invertase gene ligated to a mammalian secretory leader sequence. See, Jacobs, supra. Third, the invertase selection process is further inadequate because a certain threshold level of enzyme activity needs to be secreted to allow growth. Although 0.6–1% of wild-type invertase secretion is sufficient for growth, certain mammalian signal sequences are not capable of functioning to yield even this relatively moderate level of secretion. Kaiser, C. A. et al. (1987), *Science* 235; 312–317. As a result, there still exists the need for an improved and simplified technique for selecting genes encoding signal sequence-containing (secreted or membrane-bound) polypeptides.

SUMMARY OF THE INVENTION

The present invention concerns a novel method for identifying genes encoding secreted and membrane-bound proteins using a starch degrading enzyme as a reporter molecule. Preferably, this reporter molecule is amylolytic. More specifically, according to the present invention mammalian signal sequences are detected based upon their ability to effect the secretion of a starch degrading enzyme (e.g. amylase) lacking a functional native signal sequence. The secretion of the enzyme is monitored by the ability of the transformed yeast cells, which cannot degrade starch naturally or have been rendered unable to do so, to degrade and assimilate soluble starch.

In one embodiment, the invention relates to a method of detecting DNA comprising the coding sequence of a mammalian signal peptide which comprises:

a) screening non-amylolytic yeast cells, transformed with DNA containing the coding sequence of a mammalian signal peptide ligated to DNA encoding an amylase lacking a functional native signal peptide, for their ability to degrade starch; and b) isolating an d purifying the DNA from the cells of step a).

The yeast cells are preferably cells of a *Saccharomyces cerevisiae* strain, lacking a native amylolytic enzyme and containing an auxotrophic marker suitable for the selection of plasmid maintenance following transformation. The mammalian coding sequence is inserted amino terminal to, and in-frame with the secretion defective amylase gene. In a particularly preferred embodiment, the ATG start codon is eliminated or mutated at the N-terminus of the signal sequence as well as at the N-terminus of the mature amylase gene, such that translation is initiated only from the start codon of the mammalian signal peptide to be identified.

In another embodiment, the invention relates to a method of detecting, in a mammalian recombinant DNA library, DNA encoding a secreted or transmembrane protein or an N-terminal fragment thereof, which comprises:

a) screening non-amylolytic yeast cells, transformed with DNA obtained by the ligation of said mammalian recombinant DNA library to DNA encoding an amylase lacking a functional native signal peptide, for their ability to degrade starch; and b) isolating and purifying DNA from the cells of step a).

Just as in the previous embodiment, the yeast transformed is preferably a *Saccharomyces cerevisiae* strain, or another yeast strain lacking a native amylase gene, while the recombinant DNA library preferably is a mammalian cDNA library. The DNA identified preferably is a full-length cDNA encoding a novel secreted or transmembrane polypeptide.

It should further be appreciated that the previously enumerated embodiments may also be modified such that yeast cells which can naturally degrade starch may be employed, provided that the native amylase signal sequence has been rendered inoperable or preferably deleted prior to the ligation of the mammalian recombinant DNA library.

In yet another embodiment, the invention relates to a method of creating a cDNA library enriched in signal sequences which comprises:

a) creating a full-length cDNA library containing a first unique restriction site and a DNA promotor region 5' to the inserted cDNA;

b) transcribing an mRNA transcript from the cDNA of step a);

c) preparing random DNA oligonucleotide primers and reverse transcribing to create cDNA fragments of the full-length cDNA clone;

d) preparing the cDNA fragments of step c) for ligation, and ligating to an adapter oligonucleotide coding for a second unique restriction site;

e) digesting the cDNA of step d) with a restriction enzyme which cuts at the first unique restriction site;

f) isolating cDNA fragments which have been cut by the restriction enzyme of step e) and correspond to a size of about 500 to about 1000 base pairs in length; and g) ligating the isolating cDNA fragment of step f) into an amylase expression vector previously digested with enzymes compatible with the first and second restriction site of the cDNA of step f).

In a still further embodiment, the invention relates to a method of detecting cDNA encoding a novel secreted or transmembrane protein or an N-terminal fragment thereof in a mammalian cDNA library which comprises:

a) screening non-amylolytic yeast cells, transformed with cDNA obtained by the ligation of a mammalian cDNA library enriched for signal sequences, to DNA encoding an amylase lacking a functional native signal peptide, for their ability to degrade starch;

b) isolating and purifying cDNA from the transformed yeast cells of step a) which are capable of degrading starch; and c) analyzing the cDNA from step b) to determine novelty.

The invention further relates to a variation of the above embodiments wherein the screening method is selected from the following:

a) growth on selective media followed by replica plating onto YEPD-starch media;

b) growth on selective media wherein starch is directly incorporated; and c) growth on selective media wherein starch bonded to a visible dye is directly incorporated.

Figure 1:
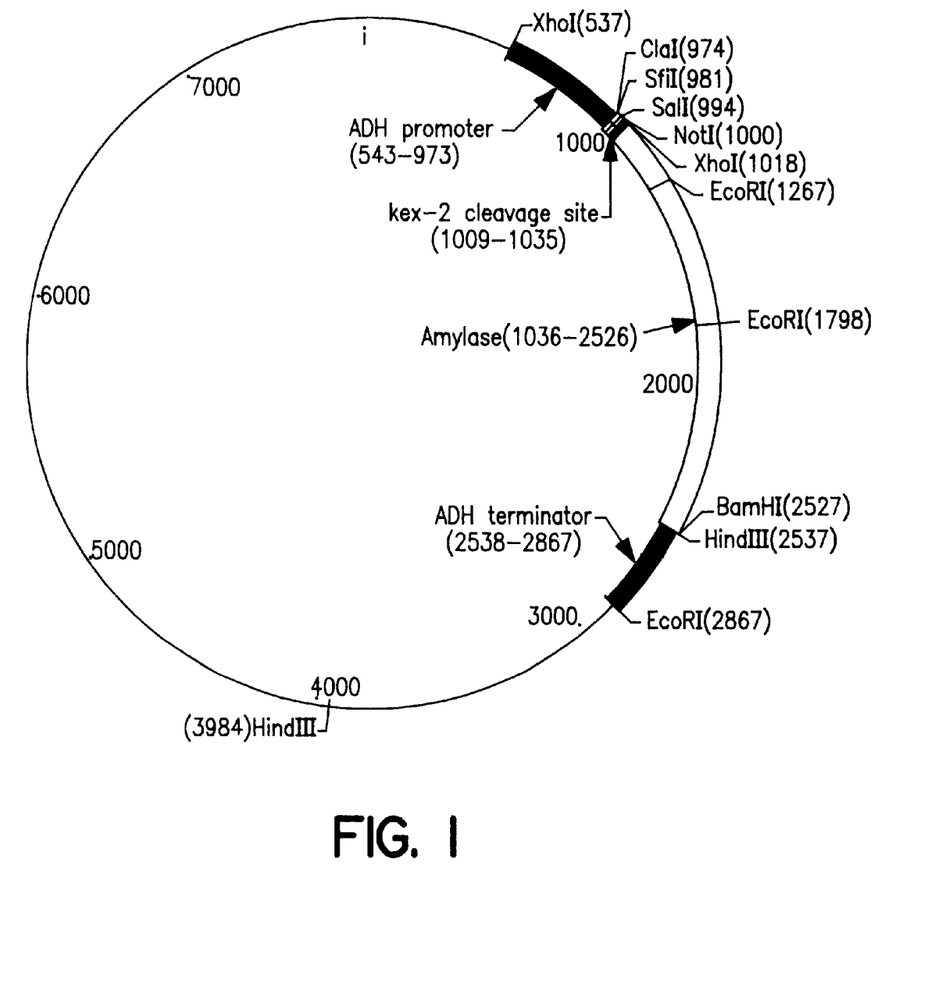
FIG. 1 represents pSST-amy.1, (SEQ ID NO:1) a yeast expression vector or plasmid preferably employed with the invention.

SEQ ID NO: 1 is the nucleotide sequence represented by the expression plasmid of FIG. 1.

SEQ ID NO:2 is the forward oligonucleotide primer used in the PCR amplification of Example 3.

SEQ ID NO:3 is the reverse oligonucleotide primer used in the PCR amplification of Example 3.

DETAILED DESCRIPTION OF THE INVENTION

Definitions

Terms employed throughout this application should be construed with their ordinary and common meanings as known to those of ordinary skill in the art. Additionally, Applicants desire that the following terms be given the following construction:

The terms "signal sequence", "signal peptide" and "secretory leader" are used interchangeably and refer to a short (usually about 15–60 amino acids), continuous stretch of amino acids at the amino-terminus of secreted and membrane-bound polypeptides, which directs their delivery to various locations outside the cytosol. Thus, specific sorting or targeting signals, which include signal sequences, may direct the delivery of polypeptides into the nucleus, ER, mitochondria, peroxisomes, etc. Signal sequences usually contain a hydrophobic core of about 4–15 amino acids, which is often immediately preceded by a basic amino acid. At the carboxyl-terminal end of the signal peptide there are a pair of small, uncharged amino acids separated by a single intervening amino acid that defines the signal peptide cleavage site. von Heijne, G. (1990) *J. Membrane Biol.* 115: 195–201. Despite their overall structural and functional similarities, native signal peptides do not have a consensus sequence.

The term "amylase" is used to refer to an amylolytic enzyme catalyzing the hydrolysis of α-D-glucosidic linkages of polysaccharides such as starch. The term specifically includes endoamylases (a.k.a. α-amylases), which are responsible for endohydrolysis of α-1,4-D-glucosidic bonds at random; exoamylases, which attacks the α-1,4-D-glucosidic linkages only from the non-reducing outer polysaccharide ends; β-amylases, which break every alternate glucosidic bond to produce maltose; and glucoamylases (a.k.a. γ-amylases), which hydrolyze terminal α-1,4-D-glucosidic linkages to produce β-D-glucose, and sometimes also α-1,6-D-glucosidic bonds (Modena et al. (1986), *Arch. Bioch. Biophys* 248: 138–150. The source of the amylase enzymes used in the present invention can be of any source, including enzymes of mammalian, e.g. human, bacterial, fungal, or plant origin, whether purified from natural sources, prepared by recombinant DNA technology, chemical synthesis or any combination of these and/or other techniques. The term "amylase", unless otherwise indicated, collectively refers to all amylases covered by this definition. Amylases are commercially available, or can be produced by conventional methods well known for those skilled in the art. The most commonly known α-amylases are those isolated from various mammalian sources, including, e.g., human saliva, human, mouse (murine), hog and rat pancreas, *Bacillus subtilis, Bacillus coagulans, Bacillus amyloliquefaciens, Bacillus licheniformis, Bacillus stearothermophilus*, various Aspergillus strains (e.g., *Aspergillus, awamori*), *Pseudomonas saccharophila, Streptomyces hygroscopicus, Streptomyces venezuelae, Streptomyces limosus, Schwanniomyces occidentalis, Saccharomycopsis fibuligera, Drosophila melanogaster, Saccharomyces diastaticus* and barley malt. *Saccharomyces cerevisiae* also produces an intracellular glucoamylase, which can be used with the present invention, but this enzyme is only produced by diploid cells undergoing sporulation. The nucleotide sequences of the human salivary and pancreatic α-amylase genes have, for example, been disclosed by Nakamura et al. (1984), *Gene* 28, 263–270, and Nishide et al. (1986) *Gene* 50, 371–372. The cloning of the α-amylase cDNA of *Aspergillus shirousamii* has been reported by Shibuya et al. (1992) *Biosci. Biotech Biochem.* 56, 174–179. The cloning of a glucoamylase from the same organism was first described in Shibuya et al. (1990) *Agric. Biol. Chem.,* 54, 1905–1914. The cloning of a glucoamylase gene of the yeast *Arxula adeninivorans* from a genomic library is reported by Bui et al. (1996), *Appl. Microbiol. Biotechnol.* 44, 610–619. Potato α-amylase genes are disclosed, for example, in U.S. Pat. No. 5,498,832, issued Mar. 12, 1996. The genes specifically mentioned are for illustration only. A large variety of additional amylase genes have been cloned and sequences from various sources, and further genes can be readily identified by similar techniques. All amylases contain a short, N-terminal signal sequence which directs their secretion. The amylase gene used in accordance with the present invention preferably is of mouse origin or is from an amylolytic yeast. (see, e.g. McCann and Barnett (1986) *Yeast* 2, 109–115).

The phrase "non-amylolytic" is used to refer to yeast cells that do not produce native amylase or in which the signal sequence(s) of the amylase(s) naturally produced has/have been deleted or inactivated, such that the native amylase is not secreted. In contrast, "amylolytic" yeast are those that can degrade starch due to the presence of one or more native secreted amylase enzymes. A typical, and preferred, representative of yeast that cannot degrade starch naturally is *Saccharomyces cerevisiae* (Baker's yeast). Many genes from bacteria, filamentous fungi and yeasts that encode amylolytic enzymes have been cloned into, and expressed in, *S. cerevisiae.* Representatives of other yeast strains lacking native amylase genes and which can be used with the present invention are *Schizosaccharomyces pombe, Hansenula polymorpha, Kluveromyces lactis* and *Pichia pastoris.* Clementi, R. & Rossi, J. (1986) *Antonie van Leeuwenhoek* 52; 343–352.

The phrase "recombinant DNA library" is used to refer collectively to genomic and cDNA libraries. Preferably, a "recombinant DNA library" contains a substantially complete representation of all genomic or cDNA sequences from a particular cell or tissue source.

The term "DNA" is used to refer collectively to genomic DNA and cDNA, prepared from any source, including bacteria, plant cells, and mammalian cells, preferably cells of high primates, most preferably humans.

The term "plate" is used to refer to petri dishes or 96-well micro titer dishes filled with solid medium used to grow separated bacterial colonies or plaques.

The terms "plating" or "plating out" refer to the placement of bacteria, phages or yeast on plates so that colonies or plaques are formed.

"Transformation" means introducing DNA into an organism so that the DNA is replicable, either as an extrachromosomal element or chromosomal integrant. Transformation is usually performed by the $CaCl_2$ transfection (Mandel and Higa, *J. Mol. Biol.* 53, 159–162 (1970)), electroporation (Miller et al., *Proc. Natl. Acad. Sci. USA* 85, 856–860 (1988), Shigekawa and Dower, *BioTechnique* 6, 742–751 (1988)), Ausubel et al., *Current Protocals in Molecular Biology,* Unit 9.3, John Wiley & Sons, Inc. (1995). DEAE-dextran technique (eukaryotic cells, Lopata et al., *Nucleic Acids Res.* 12(14):5707–5717 (1984)), and liposome-mediated transfection (Felgner et al., *Proc. Natl. Acad. Sci. USA* 84, 7413–7417 (1987)). Unless otherwise provided, the method used herein for transformation of *E. coli* is electroporation.

"Polymerase Chain Reaction" or "PCR" is a rapid procedure for in vitro enzymatic amplification of a specific DNA segment. The DNA to be amplified is denatured by heating the sample. In the presence of DNA polymerase and excess deoxynucleotide triphosphates, oligonucleotides that hybridize specifically to the target sequence prime new DNA synthesis. One round of synthesis results in new strands of indeterminate length which, like the parental strands, can hybridize to the primers upon denaturation and annealing. The second cycle of denaturation, annealing and synthesis produces two single-stranded products that together compose a discrete double-stranded product, exactly the length between the primer ends. This discrete product accumulates exponentially with each successive round of amplification. Over the course of about 20 to 30 cycles, many million-fold amplification of the discrete fragment can be achieved. PCR protocols are well known in the art, and are described in standard laboratory textbooks, e.g. Ausubel et al., supra, Unit 15.

"Reporter molecule" is a gene which codes for a protein which possess unique enzymatic ability or is otherwise easily distinguishable from the mixture of intra- or extra-cellular proteins. Typically, they are operably linked to test DNA, the transcriptional capability of which can then be estimated from the in vitro activity of the reporter gene product in the culture medium. Reporter genes and their application to mammalian gene transcription are described by Alam and Cook, (1990), *Anal. Biochem.* 188: 245–254. In the present invention, the reporter molecule is a starch degrading enzyme, which is preferably amylase.

Detailed Description

Starch is one of the most widely distributed, naturally occurring organic compound which is derived mainly from higher plants. Soloman, B. (1978) *Advances in Biochemical Engineering,* eds., Springer Berlin Heidelberg, New York, 10: 135–177. Starch comprises two major components: (1) amylose, which comprises mainly α-1,4-linked D-glucose residues; and (2) amylopectin, which comprises both α-1,4- and α-1,6-linked D-glucose residues. Jensen B. F. and Norman B. (1984), *Process Biochem.* 19: 129–134. The relative content of amylose and amylopectin in starch varies with the source. Amylose generally accounts for 20%–30% of the starch weight and has an average chain length of 500–1000 glucose units. Manners, D. J. (1989), *Carbohydr. Pol.* 11: 87–112. Amylopectin represents the major fraction of starch (70%–80%) and usually has a bimodal pattern of distribution, with shorter chains having average lengths of 11–25 and the longer chains 40–60 D-glucosyl residues, Soloman, supra. The methods of the invention work as a means of screening because starch can be broken down into its various component parts by the operation of amylase, and the presence of starch (or lack thereof) can be made readily discernable to the naked eye.

The methods of the present invention are preferably used for screening recombinant DNA libraries for the presence of novel secreted or membrane-bound proteins.

The construction of a genomic DNA library typically includes the following steps: (1) isolation of genomic DNA, (2) partial or complete digestion of the DNA, and (3) size fractionation. The DNA is then ligated to a vector, and introduced into a host cell, e.g. *E. coli* (by transformation with a plasmid vector or by in vitro packaging into bacteriophage particles and subsequent infection of *E. coli*). The latter steps are substantially the same for genomic and cDNA libraries. The size of a library of random genomic DNA fragments that is required to ensure representation of all sequences present in the genome will depend on the size of the genome and the size of the cloned fragments (see, Clarke, *Cell* 9, 91–99 (1976)). There are a number of different procedures for the preparation of genomic DNA, all of which start with some form of cell lysis, followed by deproteinization and recovery of the DNA. Typical protocols for the preparation of genomic DNA from mammalian, plant tissues and bacteria are described, e.g. in Ausubel et al., supra, Units 2.2–2.4. Digestion of the genomic DNA is performed by restriction enzymes, following routine procedures of partial or complete digestion. In order to avoid distortions, it is important to select an enzyme that cuts the DNA with high frequency but without any bias in selection of one site over another. A partial digestion method for the maximization of the randomness of DNA sequence in genomic libraries is described, for example, in Seed et al., *Gene* 19, 201–209 (1982). Protocols for enzymatic manipulation of DNA are disclosed in Ausubel et al., supra, Unit 3. The completely or partially digested DNA must then be size fractionated to remove small and large fragments, which would interfere with subsequent cloning. Methods for size fractionation are well known in the art and are typically based on sucrose gradient fractionation or preparative gel electrophoresis. The DNA is then ligated into a vector, which is introduced into a host cell, typically *E. coli*. General techniques for the construction of genomic DNA libraries are disclosed, for example, in Ausubel et al., supra, especially in Units 5.1.1–5.1.2; 5.3.2–5.3.6; 5.4.1–5.4.3; and 5.7.1–5.7.3. Introduction of the library into *E. coli* can be performed by any standard transformation techniques, including $CaCl_2$ transfection, and electroporation.

In a typical procedure of constructing recombinant cDNA libraries, poly(A)$^+$ mRNAs are isolated from cells, preferably a cell type in which the mRNA encoding the desired polypeptide is produced in large quantities. The mRNAs are then converted into double stranded cDNA (dscDNA) in vitro using the enzyme reverse transcriptase to synthesize complementary cDNA strands from the mRNA template. In order to obtain double-stranded DNA suitable for ligation into a vector, the dscDNA copy of the mRNA is methylated and equipped with suitable (usually EcoRI) linkers. Methods for methylation of DNA are well known in the art, and involve the use of commercially available methylases which covalently join methyl groups to adenine or cytosine residues within specific target sequences. For example, EcoRI methylates an adenine residue within the EcoRI recognition sequence. In the process of converting mRNA into double stranded cDNA in vitro, a first cDNA strand is synthesized by the reverse transcriptase and separated from the mRNA by treatment with alkali or using a nuclease such as the enzyme RNase H. Conveniently, this step can be achieved using a reverse transcriptase that also has RNase H activity. *E. coli* DNA polymerase then uses the first cDNA strand as a template for the synthesis of the second cDNA strand, thereby producing a population of dscDNA molecules from the original poly(A)$^+$ mRNA. After converting the 5' and 3' ends into blunt ends, the dscDNA can be ligated to linkers/adaptors and subsequently ligated into suitable vectors and transformed or packaged into a cell, thereby forming the library. For methods for preparing high-quality cDNA libraries see, for example, Gubler and Hoffman, *Gene* 25, 263–269 (1983); Okayama and Berg, *Mol. Cell. Biol.* 2, 161–170 (1982); and Kato et al., *Gene* 150, 243–250 (1994). Typical protocols for making cDNA libraries are also described in Ausubel et al., supra, especially in Units 5.2.1; 5.5.2–5.5.7; 5.6.1–5.6.8; and 5.8.1–5.8.11. A particularly advantageous method for converting mRNA into dscDNA is disclosed in copending patent application Ser. No. 08/872, 861 filed Oct. 15, 1996. According to this method, reverse transcriptase-producing cells are transformed with vectors in which the 5' end of a mRNA molecule having a 5' oligonucleotide cap is ligated to a single-stranded 5' overhang complementary to the oligonucleotide cap, and the 3' end of the mRNA molecule is ligated to a single-stranded 3' overhang complementary to the 3' end of the mRNA molecule, so that the reverse transcriptase produced by the cell converts the mRNAs into dscDNAs to form a cDNA library.

In the preferred embodiment of carrying out the present invention, a library is created which is enriched in signal sequences. This library is enriched in amino terminal signal sequences which are within a cloning vector that possesses both a unique restriction site at the 5' end of the inserted cDNA clone and a DNA promotor 5' to the inserted cDNA. Next, the cDNA clone is transcribed using the corresponding RNA polymerase to create an RNA transcript which contains the sequence of the transcribed cDNA in addition to vector sequence containing the 5' unique restriction sequence. For example, an Sp6 promotor can be used in conjunction with Sp6 polymerase or a T7 promotor with T7 polymerase. Suitable additional promoters and RNA polymerases will be apparent to one of ordinary skill in the art. The RNA sequence is then randomly primed and replicated to produce various single stranded DNA fragments. These fragments are in turn replicated into double stranded fragments and specific DNA adapters are ligated onto the ends of the DNA fragments. The adapters are used in order to convert the blunt end of the replicated terminus into an exposed 5' end, similarly to what would result if a restriction enzyme had been used. Exposed 5' ends are necessary to maximize the efficiency of T4 DNA ligase, an essential step for insertion of the cDNA fragment into the cloning vector. The ligated double stranded fragments are then digested with specificity for cutting at the unique restriction site. The DNA fragments within a defined size range may then be isolated by gel electrophoresis and cloned into restriction sites within the amylase vector that are compatible with the specific 5' unique restriction site and the DNA adapter. In this manner it is possible to identify only those DNA fragments which correspond to the 5' end of the initial cDNA within the full length library. These fragments may then be used in the next step, which is the creation of a cDNA fusion library.

The use of the above-described enriched signal sequence library offers several advantages over the prior art. First, this library ensures that all cDNA fragments which are screened in the amylase assay as containing signal sequences will be derived from specific cDNA present in the actual full-length library. If the full-length library were created completely independently from the "amylase library" or the cDNA fragments actually tested in the screen, there would be some novel genes identified through chance which were not actually represented in the retained full-length library. As a result, time and effort would be spent not only searching for a clone which doesn't exist in the full-length library, but also in searching for a full-length library which actually does contain the gene of interest.

Additionally, the enriched signal sequence library, which contains a population of mammalian cDNA which is enriched in fragments proximal to the 5' end of the cDNA insertion, provides for a greater number of functional signal sequences over that which would be obtained if the tested population were comprised of random cDNA derived from the full length cDNA. The number of selected functional signal sequences is increased because, any signal sequence, if present in the full-length library, will be proximal to the 5' end of the cDNA insertion.

The next step is the creation of a cDNA-fusion library, in which the library is fused N-terminally to an amylase gene lacking a functional signal sequence. The fusion library is created in any suitable yeast cloning vector known in the art, which carries a non-secreted amylase gene having its signal sequence deleted or inactivated. Preferably, the vector is derived from a λ phage or a filamentous phage. Vectors derived from a filamentous phage (phagemid vectors) contain an M13, f1 or fd origin of replication. Filamentous phages are very useful cloning vectors because they are suitable for packaging of any length of DNA, and permit the isolation of DNA in either single- or double-stranded form. Prototypes of filamentous phage vectors are M13 mp derivatives, that were originally developed by Messig and colleagues. M13-based cloning vectors, along with general techniques for working with them are disclosed, for example, in Messing, J. *Methods Enzymol.* 101, 20–78 (1983); and Messing et al., *Proc. Natl. Acad. Sci. USA* 74, 3642–3646 (1977). Particularly useful M13-based vectors are M13mp18 and pUC19 vectors (Xanisch Perron et al., *Gene* 33, 103–119 (1985)), pRK5-based vectors (EP 307, 247 published Mar. 15, 1989), pUC118 (Viera and Messing, *Methods Enzymol.* 153, 3–11 (1987)), pBluescribe (Stratagene), and pBluescript (Stratagene). Other phagemid vectors may contain the origins of replication of other phages, such as F1. Such vectors usually also contain a pBR322 origins of replication, a drug resistance coding gene, and a polylinker inserted in frame into the portion of the lacZ gene coding for the alpha peptide. (See, e.g. Ausubel et al., Current Protocols in Molecular Biology, John Wiley and Sons, publ. (1991), Unit 1.15.7.) Derivatives of the phage λ that are used as cloning vectors typically contain restriction sites that flank some or all of the dispensable genes in about the middle third of the λ genome. DNA can be inserted and packaged into such phages in vitro. λ phage cloning vectors are well known in the art, and are disclosed, for example, in Ausubel et al., supra, Units 1.10–1.11. Some representative λ vectors include λRK18 (Klein et al., supra); λ Max1 (Clontech); λ EMBL3, λ2001, λgt10, λgt11, Charon 4a, Charon 40, λZAP (e.g. λZAP/R, λZAP/L) the latter most 7 of which are disclosed in Ausubel et al., supra. λ-based vectors allow for efficient cloning of large numbers of cDNAs, and subsequent conversion to a plasmid library (for example in suitable bacterial cells, e.g. *E. coli*) that can be introduced into yeast.

Yeast cells may be transformed with the plasmid library obtained by any technique known in the art. For example, transformation may be performed using lithium acetate (LiAc) in TE buffer, essentially as described in Gietz et al., *Nucl. Acid. Res.* 20(6), 1425 (1992). Alternatively, efficient transformation may be achieved by using the spheroplast transformation procedure, described, for example, in Ausubel et al., supra, Unit 13.7.3. Preferably, transformation is done by electroporation, as described previously. While a *Saccharomyces cerevisiae* strain is preferably employed with the present invention, the practice and scope of this invention should not be construed as being limited exclusively to this species. Any yeast organism which natively lacks the ability to degrade starch (i.e is non-amylolytic) and which is capable of being transformed by the above listed techniques so as to be rendered capable of starch degradation is useable with this invention. For example, *Schizosaccharomyces pombe, Hansenula polymorpha, Kluveromyces lactis* and *Pichia pastoris.* Clementi, R. & Rossi, J. (1986) *Antonie van Leeuwenhoek* 52; 343–352.

Alternatively, yeast strains which naturally do produce starch degrading enzymes (i.e are amylolytic) may be employed with the present invention, provided that the natural signal sequence for such starch degrading enzyme has been inactivated. The inactivation or "knock-out" may be accomplished by any known technique commonly employed in the art, e.g. site-directed mutagenesis. Additional techniques of inactivation are described in Ausubel, Chapter 8, supra. A suitable technique typically employs inactivating the entire gene by removing a large portion of it and replacing the deletion with a selectable marker (e.g. URA3, LEU2, HIS3). This inactive gene-marker fused hybrid can then be used to replace the functional, chromosomal copy of the gene within the cell by homologous recombination following transformation. Rothstein, R. (1991) *Methods Enzymol.* 194; 281–301. Suitable amylolytic yeast strains which can be employed with this technique are described above under the definition of amylase.

After transformation, the yeast colonies are grown on selective media in order to detect the desired transformants. Detection may be effected by any technique commonly employed in the art. For example, (1) replica plating from the growth medium onto a YEPD-starch medium, (2) growth on a selective medium wherein starch was also incorporated, and (3) growth on a selective medium wherein starch is covalently attached to a readily identifiable dye.

Applicants have discovered that the replica plating step can be preferably deleted by incorporation of starch directly into the selective growth media. The elimination of the replica plating step saves considerable time and effort, since colonies typically take 7–10 days to grow in the invertase screen following replica plating. The starch concentration can also be varied in order to adjust the sensitivity of the detection screen. That is, lower starch concentrations would be expected to detect less "functional" or more weakly secreted signal sequences. Contrarily, increasing the starch concentrations lowers the sensitivity to eliminate false positives or "noise" within the detection system. Preferably, starch concentrations are varied from 0.5% to 2.0%.

The yeast colonies may be stained by any technique known in the art. For example, by exposure to iodine vapor, which can be accomplished by inverting the agar plate over iodine crystals for a time sufficient to visibly stain the starch in the plate media, e.g. 2–5 minutes. The iodine will form a blue-black staining complex with the starch present in the media, but not with the amylase break down products. In the preferred embodiment, the starch is bonded to a visible dye. When amylase is secreted by the individual colonies, a clear halo is readily identifiable without further manipulation. Any dye suitable for attachment to starch can be used, as is known in the art. The dye-starch bonding technique and useable dyes preferably employed in the invention are as identified in Biely et al. *Anal. Biochem.* 172, 176–179 (1988).

Once amylase secreting colonies have been identified, they can be restreaked across fresh selective media in order to obtain well defined single colonies. The restreaking process also ensures plasmid maintenance amongst the yeast transformants. In the preferred embodiment, which incorporates the starch directly into the selective media, we have discovered that the time for the restreaking process is diminished vis-à-vis the invertase process, e.g. 3 days v. 5–7 days.

The restreaked, transformed colonies can then be analyzed by any technique known in the art to detect novel DNA sequences. For example, isolation and purification of the DNA, then comparison to known sequences or libraries via hydribization techniques as is known. Alternatively, and preferably, the DNA present in the yeast colonies can be directly amplified by Polymerase Chain Reaction or PCR. The PCR oligos are designed to start and stop amplification of the amylase vector on either side of the inserted cDNA. The exact sequences will vary depending upon the type of amylase yeast expression vector employed. Preferably, the plasmid employed is pSST-amy.1 and the PCR oligos are sequences which anneal to the ADH promotor region and the amylase-encoding gene of the vector as recited in Example 3. However, other suitable amylase expressing vectors and marker annealing PCR oligos will be readily determinable to those of ordinary skill in the art. Amplified DNA sequences are then further isolated and analyzed by known and available techniques, such as column purification, gel electroporation and/or DNA sequencing. The cDNA may then be compared to known sequences and novelty ascertained.

The following examples are offered by way of illustration and not by way of limitation and should not be construed as limiting the invention in any way. The disclosures of all citations in the specification are expressly incorporated herein by reference.

EXAMPLES

Example I

Construction of Full-Length cDNA Library

Isolation of m-RNA

Human fetal liver mRNA was obtained from Clontech Laboratories, Inc. Palo Alto, Calif. U.S.A., catalog no. 64018-1.

The following protocol is described in "Instruction Manual: Superscript® Lamda System for cDNA Synthesis and λ cloning," cat. No. 19643-014, Life Technologies, Gaithersburg, Md., U.S.A. which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis

Not1 primer-adapter (Life Tech., 2 $\mu$l, 0.5 $\mu$g/$\mu$l) was added to a sterile 1.5 ml microcentrifuge tube to which was added poly A+ mRNA (7 $\mu$l, 5 $\mu$g). The reaction tube was heated to 70° C. for 5 minutes or time sufficient to denature the secondary structure of the mRNA. The reaction was then chilled on ice and 5× First strand buffer (Life Tech., 4 $\mu$l), 0.1 M DTT (2 $\mu$l) and 10 mM dNTP Mix (Life Tech., 1 $\mu$l) were added and then heated to 37° C. for 2 minutes to equilibrate the temperature. Superscript II® reverse transcriptase (Life Tech., 5 $\mu$l) was then added, the reaction tube mixed well and incubated at 37° C. for 1 hour, and terminated by placement on ice. The final concentration of the reactants was the following: 50 mM Tris-HCl (pH 8.3); 75 mM KCl; 3 mM $MgCl_2$; 10 mM DTT; 500 $\mu$M each dATP, dCTP, dGTP and dTTP; 50 $\mu$g/ml Not 1 primer-adapter; 5 $\mu$g (250 $\mu$g/ml) mRNA; 50,000 U/ml Superscript II® reverse transcriptase.

Second Strand Synthesis

While on ice, the following reagents were added to the reaction tube from the first strand synthesis, the reaction well mixed and allowed to react at 16° C. for 2 hours, taking care not to allow the temperature to go above 16° C.: distilled water (93 $\mu$l); 5× Second strand buffer (30 $\mu$l); dNTP mix (3 $\mu$l); 10 U/$\mu$l *E. Coli* DNA ligase (1 $\mu$l); 10 U/$\mu$l *E. Coli* DNA polymerase I (4 $\mu$l ); 2 U/$\mu$l *E. Coli* RNase H (1 $\mu$l). 10 U T4 DNA Polymerase (2 $\mu$l) was added and the reaction continued to incubate at 16° C. for another 5 minutes. The final concentration of the reaction was the following: 25 mM Tris-HCl (pH 7.5); 100 mM KCl; 5 mM $MgCl_2$; 10 mM $(NH_4)_2SO_4$; 0.15 mM β-NAD+; 250 $\mu$M each dATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 $\mu$l), then extracted through phenol:chloroform:isoamyl alcohol (25:24:1, 150 $\mu$l). The aqueous phase was removed, collected and diluted into 5M NaCl (15 $\mu$l) and absolute ethanol (-20° C., 400 $\mu$l) and centrifuged for 2 minutes at 14,000×g. The supernatant was carefully removed from the resulting DNA pellet, the pellet resuspended in 70% ethanol (0.5 ml) and centrigued again for 2 minutes at 14,000×g. The supernatant was again removed and the pellet dried in a speedvac.

Adapter Addition

The following reagents were added to the cDNA pellet from the Second strand synthesis above, and the reaction was gently mixed and incubated at 16° C. for 16 hours: distilled water (25 $\mu$l); 5× T4 DNA ligase buffer (10 $\mu$l); Sal I adapters (10 $\mu$l); T4 DNA ligase (5 $\mu$l). The final composition of the reaction was the following: 50 mM Tris-HCl (pH 7.6); 10 mM $MgCl_2$; 1 mM ATP; 5% (w/v) PEG 8000; 1 mM DTT; 200 $\mu$g/ml Sal 1 adapters; 100 U/ml T4 DNA ligase. The reaction was extracted through phenol:chloroform:isoamyl alcohol (25:24:1, 50 $\mu$l), the aqueous phase removed, collected and diluted into 5M NaCl (8 $\mu$l) and absolute ethanol (-20° C., 250 $\mu$l). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion

To the cDNA prepared with the Sal 1 adapter from the previous paragraph was added the following reagents and the mixture was incubated at 37° C. for 2 hours: DEPC-treated water (41 $\mu$l); Not 1 restriction buffer (REACT, Life Tech., 5 μl), Not 1 (4 μl). The final composition of this reaction was the following: 50 mM Tris-HCl (pH 8.0); 10 mM MgCl$_2$; 100 mM NaCl; 1,200 U/ml Not 1.

Gel Isolation of cDNA

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 μl) and extracted with phenol:chloroform:isoamyl alcohol (25:24:1, 200 μl). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 μl).

Ligation of cDNA Into pRK5 Vector

The following reagents were added together and incubated at 16° C for 16 hours: 5× T4 ligase buffer (3 μl); pRK5, XhoI, Not1 digested vector, 0.5 μg, 1 μl); cDNA prepared from previous paragraph (5 μl) and distilled water (6 μl). Subsequently, additional distilled water (70 μl) and 10 mg/ml tRNA (0.1 μl) were added and the entire reaction was extracted through phenol:chloroform:isoamyl alcohol (25:24:1). The aqueous phase was removed, collected and diluted into 5M NaCl (10 μl) and absolute ethanol (−20° C., 250 μl). This was then centrifuged for 20 minutes at 14,000× g, decanted, and the pellet resuspended into 70% ethanol (0.5 ml) and centrifuged again for 2 minutes at 14,000×g. The DNA pellet was then dried in a speedvac and eluted into distilled water (3 μl) for use in the subsequent procedure.

Transformation of Library Ligation Into Bacteria

The ligated cDNA/pRK5 vector DNA prepared previously was chilled on ice to which was added electrocompetent DH10B bacteria (Life Tech., 20 μl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (370° C.) to allow the colonies to grow. Positive colonies were then scraped off and the DNA isolated from the bacterial pellet using standard CsCl-gradient protocols. For example, Ausuble et al., 2.3.1.

Example 2

Construction of Enriched 5'-cDNA Library

The following process results in a bias of cDNA fragments which preferentially represents the 5' ends of those cDNA's contained within the previously prepared full length library of Example 1.

Linearize the Full-Length Library

10 μg of the pooled isolated full-length library plasmid DNA (41 μl) of Example 1 was combined with Not 1 restriction buffer (New England Biolabs, 5 μl) and Not 1 (New England Biolabs, 4 μl) and incubated at 37° C. for one hour. The reaction was extracted through phenol:chloroform:isoamyl alcohol (25:24:1, 50 μl), the aqueous phase removed, collected and resuspended into 5M NaCl (5 μl) and absolute ethanol (−20° C., 150 μl). This was then centrifuged for 20 minutes at 14,000×g, decanted, resuspended into 70% ethanol (0.5 ml) and centrifuged again for 2 minutes at 14,000×g. The supernatant was then removed, the pellet dried in a speedvac and resuspended in distilled water (10 μl).

Sp6 Transcripts Synthesis

The following protocol was taken from InvitroScript Cap Kit (Invitrogen). The following reagents were brought together and incubated at 37° C. for 2 hours: distilled water (3 μl); linearized DNA library (prepared previously, 1 μg, 1 μl); Ribonucleotide mix (Invitrogen, 10 μl); transcription buffer (Invitrogen, 2 μl) and Sp6 enzyme mix. The reaction was then extracted through phenol:chloroform:isoamyl alcohol (25:24:1, 50 μl) and the aqueous phase was removed, collected and resuspended into 5M NaCl (5 μl) and absolute ethanol (−20° C., 150 μl) and centrifuged for 20 minutes at 14,000×g. The pellet was then decanted and resuspended in 70% ethanol (0.5 ml), centrifuged again for 2 minutes at 14,000×g, decanted, dried in a speedvac and resuspended into distilled water (10 μl).

cDNA Production From Sp6 RNA Overview

The procedure employed was the same as that used to create the full-length cDNA library described in Example 1, except with the following noted differences:

First strand synthesis: 6 Nucleotide oligomer random primers were used to prime the first strand cDNA synthesis from the Sp6 RNA transcript in order to create random fragments of cDNA instead of priming from the poly A tail to create a long full-length cDNA.

Adapter ligation: A Sal I adapter (Life Tech.) was alternatively substituted in place of the Not 1 adapter.

Restriction enzyme digestion: Cla 1 or alternatively Sfi 1 were used in place of Not 1. This cuts at a restriction site 5' to the inserted cDNA within the full length library. As a result, only those fragments which correspond to the 5' ends of cDNA present in the full length library were identified.

Gel isolation: Fragments of cDNA corresponding in size to 500–1000 base pairs were isolated. This size range was selected because it is believed that significantly shorter fragments may generate greater numbers of fortuitous and spurious signal sequences during the yeast screen.

First Strand Synthesis

The following reagents were brought together and heated at 70° C. for 5 minutes in order to denature the secondary structure of the mRNA: Sp6 transcript prepared previously (5 μg, 7 μl); N6 primer-adapter (Life Tech., 2 μl). The reaction was halted by placement on ice and First strand buffer (Life Tech., 4 μl), 0.1 M DTT (2 μl) and dNTP mix (1 μl, 10 mM each dNTP) were added and then heated to 37° C. for 2 minutes to equilibrate the temperature. Superscript II® reverse transcriptase (Life Tech., 5 μl) was then added and the reaction incubated at 37° C. for 1 hour, then terminated by placement on ice.

Second Strand Synthesis

While on ice, the following reagents were added to the reaction tube from the first strand synthesis and then reacted at 16° C. for 2 hours: distilled water (93 μl); Second strand buffer (Life Tech., 30 μl); dNTP mix (3 μl); 10 U/μl E. Coli DNA ligase(1 μl); 10 U/μl E. Coli DNA polymerase I (4 μl); 2 U/μl E. coli RNase H (1 μl). 10 U T4 DNA Polymerase (Life Tech. added and the reaction continued to incubate at 16° C. for another 5 minutes. The reaction was halt addition of 0.5 M EDTA (10 μl) and extracted through phenol:chloroform:isoamyl alcohol (25:24:1). The aqueous phase was removed, collected then diluted into 5M NaCl (15 μl) and absolute ethanol (−20° C., 400 μl) and centrifuged for 20 minutes at 14,000×g. The DNA pellet was then decanted and resuspended in 70% ethanol (0.5 ml) and centrifuged again for 2 minutes at 14,000×g. The supernatant was then removed and the pellet dried in a speedvac.

Adapter Addition

The following reagents were added to the DNA pellet obtained from the Second strand synthesis and reaction was incubated for 16 hours at 16° C.: distilled water (25 μl); 5× T4 DNA ligase buffer (Life Tech., 10 μl); Sal 1 adapters (10 μl); T4 DNA ligase (5 μl). The reaction was extracted though phenol:chloroform:isoamyl alcohol (25:24:1, 50 μl) and the aqueous phase was removed, collected and diluted into 5M NaCl (8 μl) and absolute ethanol (−20° C., 250 μl), then centrifuged for 20 minutes at 14,000×g. The DNA pellet was decanted and suspended into 70% ethanol (0.5 ml) and centrifuged again for 2 minutes at 14,000×g. The supernatant was removed and the residue pellet dried in a speedvac.

Enzymatic Digestion

The following reagents were added to the DNA pellet obtained from the adapter addition reaction and the reaction was incubated at 37° C. for one hour: distilled water (41 μl); Cla 1 restriction buffer (New England Biolabs, 5 μl) and Cla 1 (New England Biolabs, 4 μl).

Gel Isolation of DNA

The digested DNA from the digestion procedure above was size fractionated by acrylamide gel electrophoresis on a 5% acrylamide gel. cDNA fragments greater than 500–1000 base pairs in size, as determined by comparison with known molecular weight markers, were excised from the gel. The cDNA was electroeluted from the acrylamide gel into 200 μl of 0.1×TBE buffer and extracted with phenol:chloroform:isoamyl alcohol (25:24:1, 200 μl). The aqueous phase was removed, collected and diluted by 5M NaCl (20 μl) and absolute ethanol (−20° C., 600 μl). This was centrifuged for 20 minutes at 14,000×g, decanted, resuspended in 70% ethanol (0.5 ml) and centrifuged again for 2 minutes at 14,000×g. The supernatant was removed, the pellet dried in a speedvac and resuspended into distilled water (15 μl).

Ligation Into pSST-amy.1 Vector

The following reagents were added together and incubated at 16° C. for 16 hours: 5× T4 ligase buffer (Life Tech., 3 μl); pRK5 Cla-Sal digested vector, 0.5 μg, 1 μl); cDNA prepared from the digestion (5 μl); distilled water (6 μl). Subsequently, additional distilled water (70 μl) and 10 mg/ml tRNA (0.1 μl) was added and the entire reaction was extracted through phenol:chloroform:isoamyl alcohol (25:24:1, 100 μl). The aqueous phase was removed, collected and diluted by 5M NaCl (10 μl) and absolute ethanol (−20° C., 250 μl) and centrifuged for 20 minutes at 14,000× g. The DNA pellet was decanted, resuspended into 70% ethanol (0.5 ml) and centrifuged again for 2 minutes at 14,000×g. The supernatant was removed and the residue pellet was dried in a speedvac and resuspended in distilled water (3 μl).

Transformation

The ligated cDNA/pSST-amy.1 vector DNA prepared previously was chilled on ice to which was added electrocompetent DH10B bacteria (Life Tech., 20 μl). The bacteria vector mixture was then electroporated as recommended by the manufacturer. Subsequently, SOC media (Life Tech., 1 μl) was added and the mixture was incubated at 37° C. for 30 minutes. The transformants were then plated onto 20 standard 150 mm LB plates containing ampicillin and incubated for 16 hours (370° C.). Positive colonies were scraped off the plates and the DNA was isolated from the bacterial pellet using standard protocols, e.g. CsCl-gradient, Ausubel, Unit 2.3. The purified DNA was then carried on to the yeast protocols of Example 3.

Example 3

Overview: The yeast methods employed in the present invention were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

While any yeast strain containing a stable mutant ura3 is useable with the present invention, the preferable yeast strain used with the practice of the invention was HD56-5A (ATCC-90785). This strain had the following genotype: MAT alpha, ura3-52, leu2-3, leu2-112, his3-11, his3-15, MAL$^+$, SUC$^+$, GAL$^+$. Because this strain was MAL$^+$, that is, it could use maltose as a sole carbon energy source, amylase was tested for whether it could be used as a selectable marker. However, we found insufficient secretion of amylase in combination with maltose activity to support colony growth in the absence of glucose. Instead, the detection of amylase secretion alone became the selection criteria.

Transformation: Transformation was performed based on the protocol outlined by Gietz, D. et al., *Nucl. Acid. Res.* 20, 1425 (1992). With this procedure, we obtained transformation efficiencies of approximately 1×10$^5$ transformants per microgram of DNA. Transformed cells were then inoculated from agar into YEPD complex media broth (100 ml) and grown overnight at 30° C. The YEPD broth was prepared as described in Kaiser et al., *Methods in Yeast Genetics,* Cold Spring Harbor Press, Cold Spring Harbor, N.Y., U.S.A., p. 207 (1994). The overnight culture was then diluted to about 2×10$^6$ cells/ml (approx. OD$_{600}$=0.1) into fresh YEPD broth (500 ml) and regrown to 1×10$^7$ cells/ml (approx. OD$_{600}$= 0.4–0.5). This usually took about 3 hours to complete.

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM Li$_2$OOCCH$_3$), and resuspended into LiAc/TE (2.5 ml).

Transformation took place by mixing the prepared cells (100 μl) with freshly denatured single stranded salmon testes DNA (Lofstrand Labs, Gaithersburg, Md., U.S.A.) and transforming DNA (1 μg, vol. <10 μl) in microfuge tubes. The mixture was mixed briefly by vortexing, then 40% PEG/TE (600 μl, 40% polyethylene glycol-4000, 10 mM Tris-HCl, 1 mM EDTA, 100 mM Li$_2$OOCCH$_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics,* Cold Spring Harbor Press, Cold Spring Harbor, N.Y., U.S.A., p. 208–210) (1994). Transformants were grown at 30° C. for 2–3 days.

Detection of clones containing secreted proteins: The detection of colonies secreting amylase was performed by any of the several methods: (1) Replica plating onto YEPD-starch agar; (2) Selective media growth including starch; (3)

Selective media growth including red starch. The invention is preferably practiced by the latter of the following three described techniques.

Replica plating: After growth on the SCD-Ura agar was complete, the transformants were transferred by replica plating onto YEPD agar containing 2.0% (w/v) soluble potato starch (Sigma). Following the replica plating step, the colonies were allowed to regrow at 30° C. for 24–48 hours. Colonies in which amylase was secreted by signal sequences were detected by inverting the agar plate containing the colonies over exposed iodine crystals for 2–5 minutes. The iodine formed a blue-black staining complex with the starch present in the media, but not with the amylase break down products. The amylase secreting colonies, and ergo secreted proteins or signal sequence containing cDNA's were identified by a distinct halo of non-stained agar around the positive colony.

Starch concentrations in the YEPD agar was varied between 2.0% and 0.5% (w/v) and it was discovered that these starch concentrations could differentiate cells secreting amylase from those not secreting amylase.

Selective media growth including starch: Starch was also directly incorporated into the SCD-Ura agar at concentrations of 2.0%, 1.0% and 0.5% (w/v) and it was discovered that amylase secreting positives were detected provided that the media was buffered to a final pH of 7.0 with a potassium phosphate buffering system (final concentration 50 or 100 mM). This effectively eliminated the replica plating step. Buffering was necessary because the optimum pH for the mouse pancreatic amylase used in this example was 7.0 and the yeast media often is or becomes acidic due to the fermentation of glucose by the yeast.

Selective media growth including red starch: Starch was coupled to the red dye (Reactive Red-120, Sigma) as per the procedure described by Biely et al, *Anal. Biochem.* 172, 176–179 (1988). The coupled starch was incorporated into the SCD-Ura agar plates at a final concentration of 0.15% (w/v), and was buffered with potassium phosphate to a pH of 7.0 (50–100 mM final concentration). The use of the red starch eliminated both the replica plating step as well as the need to perform any staining—the positive colonies were readily distinguishable without any further manipulation.

The positive colonies from any of the above three detection methods were picked and streaked across fresh selective media (onto 150 mm plates) in order to obtain well isolated and identifiable single colonies. This step also ensured maintenance of the plasmid amongst the transformants. Well isolated single colonies positive for amylase secretion were detected either by replica plating onto YEPD/Starch agar, or by direct incorporation of starch or red starch into buffered SCD-Ura agar. Positive colonies were determined by their ability to break down starch resulting in a clear halo around the positive colony visualized either directly (red starch) or following iodine staining of the starch.

Isolation of DNA by PCR Amplification: When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTPs (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

5'-TGTAAAACGACGGCCAG TTAAATAGACCTGCAATTATTAATCT-3' [SEQ ID NO: 2]

The sequence of reverse oligonucleotide 2 was:

5'-CAGGAAACAGCTATGACC ACCTGCACACCTGCAAATCCATT-3' [SEQ ID NO: 3]

PCR was then performed as follows:

| a. | | Denature | 92° C., | 5 minutes |
|---|---|---|---|---|
| b. | 3 cycles of | Denature | 92° C., | 30 seconds |
| | | Anneal | 59° C., | 30 seconds |
| | | Extend | 72° C., | 60 seconds |
| c. | 3 cycles of | Denature | 92° C., | 30 seconds |
| | | Anneal | 57° C., | 30 seconds |
| | | Extend | 72° C., | 60 seconds |
| d. | 25 cycles of | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY1 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose using a Tris-Borate-EDTA (TBE) buffering system as described by Sambrook, J. et al., "Molecular Cloning—A Laboratory Manual" second edition, Cold Spring Harbor Laboratory Press, Cold Spring Harbor, N.Y., U.S.A. Clones resulting in a single strong PCR product larger than 400 bp were further analyzed by DNA sequencing after purification with a 96 Qiaquick PCR clean-up column (Qiagen Inc., Chatsworth, Calif., U.S.A.).

Using the procedures outlines in Examples 1–3 cDNA signal sequences were isolated and identified by known DNA sequencing. The identities and frequency of occurrence of each sequence is reported in Table 1.

TABLE 1

Identified isolated protein from amylase screen of Example 1–3

| PROTEIN | Number of Isolates | Frequency (%) |
|---|---|---|
| albumin | 75 | 33.1 |
| fibrinogen beta | 62 | 27.4 |
| novel sequences | 38 | 16.8 |
| α-fetoprotein | 12 | 5.3 |
| traG (*E. Coli*) | 6 | 2.6 |
| vit. D binding protein | 4 | 1.7 |
| heparin perenchall growth f. | 3 | 1.3 |
| archain | 3 | 1.3 |
| fibrinogen alpha | 2 | 0.8 |
| fibrinogen rel. protein | 2 | 0.8 |
| heparin cofactor II | 1 | 0.4 |
| kininogen | 1 | 0.4 |
| fibrinogen gamma | 1 | 0.4 |
| compl. factor h-like | 1 | 0.4 |
| α-1 antitrypsin | 1 | 0.4 |
| aminopeptidase A | 1 | 0.4 |
| HGF activator-like | 1 | 0.4 |
| β-2-glycoprotein | 1 | 0.4 |
| uracil DNA glycoprotein | 1 | 0.4 |
| eryth. 50 kD glycoprotein | 1 | 0.4 |
| fragile X homolog | 1 | 0.4 |

TABLE 1-continued

Identified isolated protein from amylase screen of Example 1–3

| PROTEIN | Number of Isolates | Frequency (%) |
|---|---|---|
| neurotensin N | 1 | 0.4 |
| C-reactive protein | 1 | 0.4 |
| adrenomedullin | 1 | 0.4 |
| inter-α-trypsin inhibitor | 1 | 0.4 |
| mitochondrial COX-1 | 1 | 0.4 |
| GST1 GTP binding protein | 1 | 0.4 |
| ribosomal protein s23 | 1 | 0.4 |

Example 4

Using the procedure published in Klein et al. describing the invertase selection process, signal sequences were detected, subject to DNA sequencing, and their identities and frequency of occurrence are reported in Table 2.

TABLE 2

Identified protein from invertase selection of Example 4

| PROTEIN | Number of Isolates | Frequency (%) |
|---|---|---|
| albumin | 76 | 50.6 |
| β-2-glycoprotein | 27 | 18.0 |
| fibrinogen beta | 14 | 9.3 |
| novel | 8 | 5.3 |
| kininogen | 8 | 5.3 |
| afamin | 2 | 1.3 |
| M130 antigen | 2 | 1.3 |
| heparin parench. growth f. | 2 | 1.3 |
| heparin cofactor ii | 2 | 1.3 |
| hemopexin | 1 | 0.6 |
| complement factor I | 1 | 0.6 |
| α-1 anti-trypsin | 1 | 0.6 |
| apolipoprotein B1 | 1 | 0.6 |
| α-2-hs-glycoprotein | 1 | 0.6 |
| fibrinogen gamma | 1 | 0.6 |
| α-fetoprotein | 1 | 0.6 |

TABLE 2-continued

Identified protein from invertase selection of Example 4

| PROTEIN | Number of Isolates | Frequency (%) |
|---|---|---|
| tumor protein p21 | 1 | 0.6 |
| ribosomal protein s15 | 1 | 0.6 |

In comparing Tables 1 & 2, it will be noted that the amylase screen identified 315 positives from $1.6 \times 10^6$ Ura$^+$ colonies, or a frequency of 1 in 5000. Among these, it was possible to sequence and identify 226 of these clones. In the invertase selection process, 272 Suc$^+$ positives were identified from $8 \times 10^6$ Ura$^+$ colonies, or a frequency of 1 in 29,000. From the invertase selection assay, it was possible to sequence 150 clones.

Figure 2:
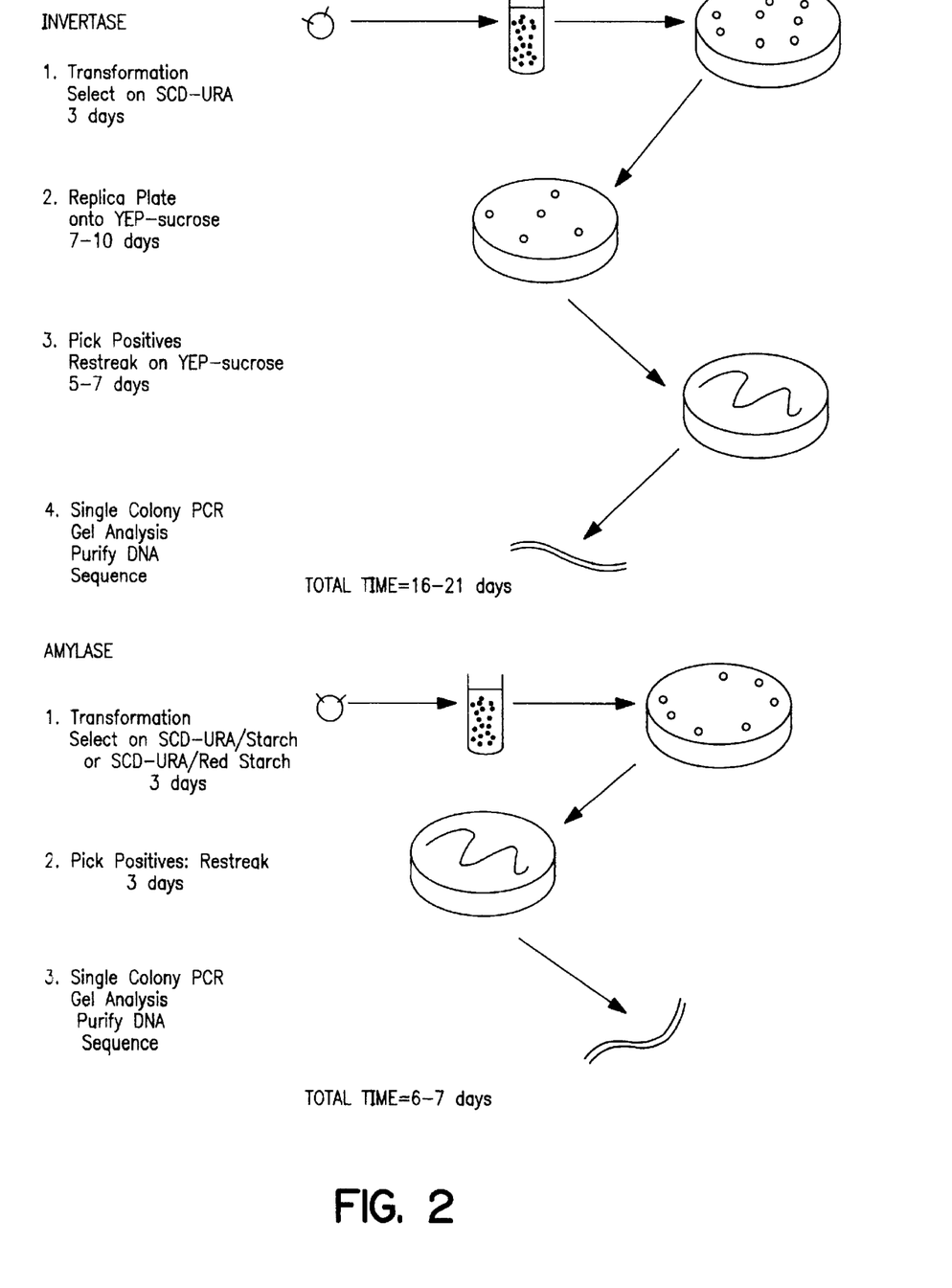
FIG. 2 represents diagrammatically a comparison between the yeast screening process of the invention and the invertase selection process of the prior art.
Figure 3:
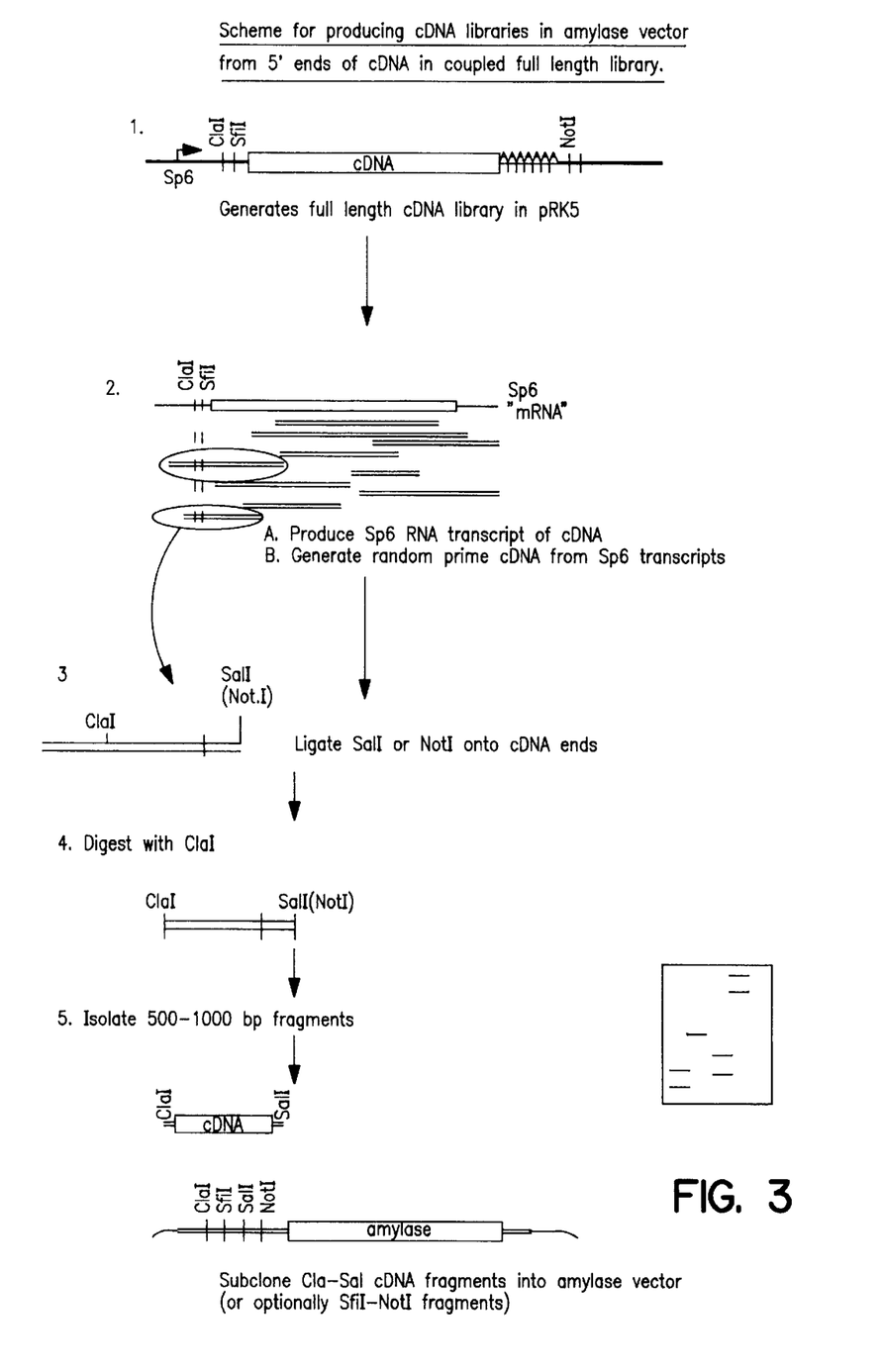
FIG. 3 represents diagrammatically the preferred embodiment encompassing the method for creating an enriched c-DNA library.

As a result, it is clear that the method of the invention as practiced above resulted in a system which is about 6-fold more sensitive than the prior art method. Moreover, this increased sensitivity occurred with about 4 fold fewer organisms screened. Furthermore, as is indicated on FIG. 2, while the prior art screening method can take up to 21 days, the present invention may be completed in as few as 6 days. This translates to over a 3 fold decrease in time of completion of the screening procedure.

Moreover, a comparison of Tables 1 and 2 indicates a larger diversity of proteins identified with amylase than with invertase. This ultimately results in 16% of the sequences obtained from the amylase screen being novel rather than the 5% obtained with invertase. The amylase process has eliminated the need for a replica plating step. Once the preliminary transformations have been performed, the positives can be directly identified; there is no need to either replica plate the transformants or to scrape and pool them prior to retesting for the invertase phenotype. This represents a considerable reduction in the time and resources necessary to complete the signal sequence analysis.

What is claimed is:

1. A method of creating a cDNA library enriched in signal sequences which comprises:
 a) creating a full-length cDNA library comprised of cDNA cloning vectors containing both a first unique restriction site and a DNA promoter located 5' to a full-length cDNA;
 b) transcribing mRNA transcripts from the cDNA cloning vectors of the cDNA library;
 c) preparing random DNA oligonucleotide primers and reverse transcribing the mRNA transcripts to create cDNA fragments of the cDNA cloning vectors of the cDNA library;
 d) preparing the cDNA fragments of step c) for ligation, and ligating the cDNA fragments to an adapter oligonucleotide containing a second unique restriction site;
 e) digesting the adapter ligated cDNA fragments of step d) with a restriction enzyme which cuts at the first unique restriction site;
 f) isolating the digested cDNA fragments of step e) which are about 500 to 1000 base pairs in length; and
 g) ligating the isolated, digested cDNA fragments of step f) into an amylase expression vector previously digested so as to also contain the first and second unique restriction sites.

2. The method of claim 1 wherein the promoter is an Sp6 promoter.

3. The method of claim 1 wherein the promoter is a T7 promoter.

4. The method of claim 1 wherein the ligating is done using T4 DNA ligase.

5. The method of claim 1 wherein the first unique restriction site is a ClaI restriction site.

6. The method of claim 1 wherein the first unique restriction site is an SfiI restriction site.

7. The method of claim 1 wherein the second unique restriction site is a NotI restriction site.

8. The method of claim 1 wherein the second restriction site is a SalI restriction site.

* * * * *

SEQUENCE LISTING

```
<160> NUMBER OF SEQ ID NOS:  3

<210> SEQ ID NO 1
<211> LENGTH: 7633
<212> TYPE: DNA
<213> ORGANISM: Artificial
<220> FEATURE:
<221> NAME/KEY: Artificial Sequence
<222> LOCATION: 1-7633
<223> OTHER INFORMATION: Amylase yeast expression plasmid

<400> SEQUENCE: 1
gccggctttc cccgtcaagc tctaaatcgg gggctccctt tagggttccg         50
atttagtgct ttacggcacc tcgaccccaa aaaacttgat tagggtgatg        100
gttcacgtag tgggccatcg ccctgataga cggttttttcg ccctttgacg       150 ttggagtcca cgttctttaa tagtggactc ttgttccaaa ctggaacaac        200
actcaaccct atctcggtct attctttttga tttataaggg attttgccga       250
tttcggccta ttggttaaaa aatgagctga tttaacaaaa atttaacgcg        300
```

-continued

```
aattttaaca aaatattaac gcttacaatt tccattcgcc attcaggctg        350
cgcaactgtt gggaagggcg atcggtgcgg gcctcttcgc tattacgcca        400
gctggcgaaa gggggatgtg ctgcaaggcg attaagttgg gtaacgccag        450
ggttttccca gtcacgacgt tgtaaaacga cggccagtga attgtaatac        500
gactcactat agggcgaatt gggtaccggg ccccccctcg aggcttagcg        550
atgcttcgtt gcttgcatgc aacttctttt cttttttttt cttttctctc        600
tcccccgttg ttgtctcacc atatccgcaa tgacaaaaaa aatgatggaa        650
gacactaaag gaaaaaatta acgacaaaga cagcaccaac agatgtcgtt        700
gttccagagc tgatgagggg tatcttcgaa cacacgaaac ttttccttc         750
cttcattcac gcacactact ctctaatgag caacggtata cggccttcct        800
tccagttact tgaatttgaa ataaaaaaag tttgccgctt tgctatcaag        850
tataaataga cctgcaatta ttaatctttt gtttcctcgt cattgttctc        900
gttccctttc ttccttgttt cttttctgc acaatatttc aagctatacc         950
aagcatacaa tcaactccaa gctatcgata ggccacactg gccgtcgacg       1000
cggccgctgg ggtatctctc gagaaaagag aggcccaata tgacccacat       1050
actcaatatg gacgaactgc tattatccac ctgtttgagt ggcgctgggt       1100
tgatattgct aaggaatgtg agagatactt agctcctaat ggatttgcag       1150
gtgtgcaggt ctctccaccc aatgaaaaca tcgtagtcca cagcccttca       1200
agaccatggt gggaaagata tcaaccaatt agctacaaaa tatgttccag       1250
gtctggaaat gaagatgaat tcagggacat ggtgaacagg tgcaacaatg       1300
ttggtgtccg tatttatgtg gatgctgtca ttaaccacat gtgtggagtg       1350
ggggctcaag ctgacaaag cagtacatgt ggaagttatt caacccaaa         1400
taacagggac tttcctggag ttccctattc tggttttgac tttaatgatg       1450
gaaaatgtag aactgcaagt ggaggtatcg agaactacca agatgctgct       1500
caggtcagag attgtcgtct gtctggcctt ctggatcttg cacttgagaa       1550
agattatgtt cgaaccaagg tggctgacta tatgaaccat ctcattgaca       1600
ttggcgtagc agggttcaga cttgatgctt ctaagcacat gtggcctgga       1650
gacataaagg caattttgga caaactgcat aatctcaata caaatggttt       1700
ctcccaagga agcagacctt tcattttcca agaggtgatt gatctgggtg       1750
gtgaggcagt gtcaagtaat gagtattttg gaaatggccg tgtgacagaa       1800
ttcaaatatg gagcaaaatt gggcaaagtt atgcgcaagt gggatggaga       1850
aaagatgtcc tacttaaaga actggggaga aggttgggt ttgatgcctt        1900
ctgacagagc ccttgtgttt gtggacaacc atgacaatca gcgaggacat       1950
ggtgctgggg gagcatccat cttgacattc tgggatgcta gactctataa       2000
aatggctgtt ggctttatgt tggctcatcc ttatggtttc acacgggtga       2050
tgtcaagtta ctattggcca agaaatttcc agaatggaaa agatgtcaat       2100
gactgggttg gaccaccaaa taacaatgga aaaccaaag aagtgagcat        2150
taacccagac agcacttgtg gcaatgactg gatctgtgaa caccgatggc       2200
gtcaaataag gaacatggtt gccttcagaa atgtcgtcaa tggtcagcct       2250
tttgcaaact ggtgggataa tgacagcaac caggtagctt ttggcagagg       2300
```

```
aaacaaagga ctcattgtct ttaacaatga tgactgggct ttgtcagaaa        2350
ctttacagac tggtcttcct gctggcacat actgtgatgt catttctgga        2400
gataaagtcg atggcaattg cactggaata aaagtctatg ttggcaatga        2450
tggcaaagct cacttttcta ttagtaactc tgccgaagac ccatttattg        2500
caatccatgc agagtcaaaa atataaggat ccgcggaagc tttggacttc        2550
ttcgccagag gtttggtcaa gtctccaatc aaggttgtcg gcttgtctac        2600
cttgccagaa atttacgaaa agatggaaaa gggtcaaatc gttggtagat        2650
acgttgttga cacttctaaa taagcgaatt tcttatgatt tatgattttt        2700
attattaaat aagttataaa aaaataagt gtatacaaat tttaaagtga         2750
ctcttaggtt ttaaaacgaa aattcttgtt cttgagtaac tctttcctgt        2800
aggtcaggtt gctttctcag gtatagcatg aggtcgctct tattgaccac        2850
acctctaccg gcatgcgaat tcgagctcgg tacccgggta ataactgata        2900
taattaaatt gaagctctaa tttgtgagtt tagtatacat gcatttactt        2950
ataatacagt ttttagttt tgctggccgc atcttctcaa atatgcttcc         3000
cagcctgctt ttctgtaacg ttcaccctct accttagcat cccttccctt        3050
tgcaaatagt cctcttccaa caataataat gtcagatcct gtagagacca        3100
catcatccac ggttctatac tgttaccca atgcgtctcc cttgtcatct         3150
aaacccacac cgggtgtcat aatcaaccaa tcgtaacctt catctcttcc        3200
acccatgtct ctttgagcaa taaagccgat aacaaaatct ttgtcgctct        3250
tcgcaatgtc aacagtaccc ttagtatatt ctccagtaga tagggagccc        3300
ttgcatgaca attctgctaa catcaaaagg cctctaggtt cctttgttac        3350
ttcttctgcc gcctgcttca aaccgctaac aatacctggg cccaccacac        3400
cgtgtgcatt cgtaatgtct gcccattctg ctattctgta tacacccgca        3450
gagtactgca atttgactgt attaccaatg tcagcaaatt ttctgtcttc        3500
gaagagtaaa aaattgtact tggcggataa tgcctttagc ggcttaactg        3550
tgccctccat ggaaaaatca gtcaagatat ccacatgtgt ttttagtaaa        3600 caaatttttgg gacctaatgc ttcaactaac tccagtaatt ccttggtggt       3650
acgaacatcc aatgaagcac acaagtttgt ttgcttttcg tgcatgatat        3700
taaatagctt ggcagcaaca ggactaggat gagtagcagc acgttcctta        3750
tatgtagctt tcgacatgat ttatcttcgt ttcctgcagg ttttgttct         3800 gtgcagttgg gttaagaata ctgggcaatt tcatgtttct tcaacactac        3850
atatgcgtat atataccaat ctaagtctgt gctccttcct tcgttcttcc        3900
ttctgttcgg agattaccga atcaaaaaaa tttcaaggaa accgaaatca        3950 aaaaaagaa taaaaaaaa atgatgaatt gaaaagctta catttatgt           4000 tagctggtgg actgacgcca gaaaatgttg gtgatgcgct tagattaaat        4050
ggcgttattg tgttgatgt aagcggaggt gtggagacaa atggtgtaaa         4100
agactctaac aaaatagcaa atttcgtcaa aaatgctaag aaataggtta        4150
ttactgagta gtatttatttt aagtattgtt tgtgcacttg cctgcaggcc       4200
ttttgaaaag caagcataaa agatctaaac ataaaatctg taaaataaca        4250
```

```
agatgtaaag ataatgctaa atcatttggc tttttgattg attgtacagg         4300
aaaatataca tcgcagggg ttgactttta ccatttcacc gcaatggaat          4350
caaacttgtt gaagagaatg ttcacaggcg catacgctac aatgacccga         4400
ttcttgctag cctttctcg gtcttgcaaa caaccgccaa ctctaagagg          4450
tgatacttat ttactgtaaa actgtgacga taaaaccgga aggaagaata         4500
agaaaactcg aactgatcta taatgcctat tttctgtaaa gagtttaagc         4550
tatgaaagcc tcggcatttt ggccgctcct aggtagtgct ttttttccaa         4600
ggacaaaaca gtttcttttt cttgagcagg ttttatgttt cggtaatcat         4650
aaacaataaa taattattt catttatgtt taaaaataaa aataaaaaa           4700 gtattttaaa ttttaaaaa agttgattat aagcatgtga cctttgcaa           4750 gcaattaaat tttgcaattt gtgatttag gcaaaagtta caatttctgg          4800
ctcgtgtaat atatgtatgc taaagtgaac ttttacaaag tcgatatgga         4850
cttagtcaaa agaaattttc ttaaaaatat atagcactag ccaatttagc         4900
acttctttat gagatatatt atagactta ttaagccaga tttgtgtatt          4950
atatgtattt acccggcgaa tcatggacat acattctgaa ataggtaata         5000
ttctctatgg tgagacagca tagataacct aggatacaag ttaaaagcta         5050 gtactgttt gcagtaattt tttctttt tataagaatg ttaccaccta           5100
aataagttat aaagtcaata gttaagtttg atatttgatt gtaaaatacc         5150
gtaatatatt tgcatgatca aaaggctcaa tgttgactag ccagcatgtc         5200
aaccactata ttgatcaccg atatatggac ttccacacca actagtaata         5250
tgacaataaa ttcaagatat tcttcatgag aatggcccag ctgcctcgcg         5300
cgtttcggtg atgacggtga aaacctctga cacatgcagc tcccggagac         5350
ggtcacagct tgtctgtaag cggatgccgg gagcagacaa gcccgtcagg         5400
gcgcgtcagc gggtgttggc gggtgtcggg gcgcagccat gacccagtca         5450
cgtagcgata gcggagtgta tactggctta actatgcggc atcagagcag         5500
attgtactga gagtgcacca tatgcggtgt gaaataccgc acagatgcgt         5550
aaggagaaaa taccgcatca ggcgctcttc cgcttcctcg ctcactgact         5600
cgctgcgctc ggtcgttcgg ctgcggcgag cggtatcagc tcactcaaag         5650
gcggtaatac ggttatccac agaatcaggg gataacgcag gaaagaacat         5700
gtgagcaaaa ggccagcaaa aggccaggaa ccgtaaaaag gccgcgttgc         5750
tggcgttttt ccataggctc cgcccccctg acgagcatca caaaaatcga         5800
cgctcaagtc agaggtggcg aaacccgaca ggactataaa gataccaggc         5850
gtttccccct ggaagctccc tcgtgcgctc tcctgttccg accctgccgc         5900
ttaccggata cctgtccgcc tttctccctt cgggaagcgt ggcgctttct         5950
catagctcac gctgtaggta tctcagttcg gtgtaggtcg ttcgctccaa         6000
gctgggctgt gtgcacgaac ccccgttca gcccgaccgc tgcgccttat          6050
ccggtaacta tcgtcttgag tccaacccgg taagacacga cttatcgcca         6100
ctggcagcag ccactggtaa caggattagc agagcgaggt atgtaggcgg         6150
tgctacagag ttcttgaagt ggtggcctaa ctacggctac actagaagga         6200
cagtatttgg tatctgcgct ctgctgaagc cagttacctt cggaaaaaga         6250
```

```
gttggtagct cttgatccgg caaacaaacc accgctggta gcggtggttt         6300
ttttgtttgc aagcagcaga ttacgcgcag aaaaaaagga tctcaagaag         6350
atcctttgat cttttctacg gggtctgacg ctcagtggaa cgaaaactca         6400
cgttaaggga ttttggtcat gagattatca aaaaggatct tcacctagat         6450
ccttttaaat taaaaatgaa gttttaaatc aatctaaagt atatatgagt         6500
aaacttggtc tgacagttac caatgcttaa tcagtgaggc acctatctca         6550
gcgatctgtc tatttcgttc atccatagtt gcctgactcc ccgtcgtgta         6600
gataactacg atacgggagg gcttaccatc tggccccagt gctgcaatga         6650
taccgcgaga cccacgctca ccggctccag atttatcagc aataaaccag         6700
ccagccggaa gggccgagcg cagaagtggt cctgcaactt tatccgcctc         6750
catccagtct attaattgtt gccgggaagc tagagtaagt agttcgccag         6800
ttaatagttt cgcaacgtt gttgccattg ctgcaggcat cgtggtgtca          6850
cgctcgtcgt ttggtatggc ttcattcagc tccggttccc aacgatcaag         6900
gcgagttaca tgatccccca tgttgtgcaa aaaagcggtt agctccttcg         6950
gtcctccgat cgttgtcaga agtaagttgg ccgcagtgtt atcactcatg         7000
gttatggcag cactgcataa ttctcttact gtcatgccat ccgtaagatg         7050
cttttctgtg actggtgagt actcaaccaa gtcattctga aatagtgta          7100 tgcggcgacc gagttgctct tgcccggcgt caacacggga taataccgcg         7150
ccacatagca gaactttaaa agtgctcatc attggaaaac gttcttcggg         7200
gcgaaaactc tcaaggatct taccgctgtt gagatccagt tcgatgtaac         7250
ccactcgtgc acccaactga tcttcagcat cttttacttt caccagcgtt         7300
tctgggtgag caaaaacagg aaggcaaaat gccgcaaaaa agggaataag         7350
ggcgacacgg aaatgttgaa tactcatact cttccttttt caatattatt         7400
gaagcattta tcagggttat tgtctcatga gcggatacat atttgaatgt         7450
atttagaaaa ataaacaaat aggggttccg cgcacatttc cccgaaaagt         7500
gccacctgac gcgccctgta gcggcgcatt aagcgcggcg ggtgtggtgg         7550
ttacgcgcag cgtgaccgct acacttgcca gcgccctagc gcccgctcct         7600
ttcgctttct tcccttcctt tctcgccacg ttc                           7633

<210> SEQ ID NO 2
<211> LENGTH: 43
<212> TYPE: DNA
<213> ORGANISM: Artificial
<220> FEATURE:
<221> NAME/KEY: Artificial Sequence
<222> LOCATION: 1-43
<223> OTHER INFORMATION: Forward PCR oligonucleotide primer

<400> SEQUENCE: 2
tgtaaaacga cggccagtta aatagacctg caattattaa tct                43

<210> SEQ ID NO 3
<211> LENGTH: 41
<212> TYPE: DNA
<213> ORGANISM: Artificial
<220> FEATURE:
<221> NAME/KEY: Artificial Sequence
<222> LOCATION: 1-41
```

-continued

```
<223> OTHER INFORMATION: Reverse PCR oligonucleotide primer

<400> SEQUENCE: 3
caggaaacag ctatgaccac ctgcacacct gcaaatccat t                              41
```